(12) United States Patent
Geisz et al.

(10) Patent No.: US 10,357,283 B2
(45) Date of Patent: Jul. 23, 2019

(54) METHOD AND SYSTEM FOR DETERMINING PRESSURE AND FLOW RESTRICTIONS IN A BODY CAVITY USING A TROCAR

(71) Applicant: Lexion Medical, LLC, St. Paul, MN (US)

(72) Inventors: Carl M. Geisz, Edina, MN (US); Rochelle M. Amann, Mendota Heights, MN (US)

(73) Assignee: Lexion Medical, Inc., St. Paul, MN (US)

( * ) Notice: Subject to any disclaimer, the term of this patent is extended or adjusted under 35 U.S.C. 154(b) by 78 days.

(21) Appl. No.: 15/398,188

(22) Filed: Jan. 4, 2017

(65) Prior Publication Data

US 2018/0185062 A1    Jul. 5, 2018

(51) Int. Cl.
  *A61B 17/34* (2006.01)
  *A61B 90/00* (2016.01)
  *A61M 13/00* (2006.01)

(52) U.S. Cl.
  CPC ....... *A61B 17/3474* (2013.01); *A61M 13/003* (2013.01); *A61B 2090/064* (2016.02); *A61M 2205/3344* (2013.01)

(58) Field of Classification Search
  CPC ......... A61B 17/3474; A61B 2090/064; A61M 13/003; A61M 13/006; A61M 2205/3344
  See application file for complete search history.

(56) References Cited

U.S. PATENT DOCUMENTS

| | | | |
|---|---|---|---|
| 5,209,721 A | 5/1993 | Wilk | |
| 5,389,077 A | 2/1995 | Melinyshyn | |
| 5,427,114 A | 6/1995 | Colliver | |
| 6,295,877 B1 | 10/2001 | Aboul-Hosn | |
| 6,299,592 B1 | 10/2001 | Zander | |
| 6,905,489 B2 | 6/2005 | Mantell | |
| 7,285,112 B2 * | 10/2007 | Stubbs | A61B 17/3421 128/898 |
| 7,722,558 B2 | 5/2010 | Ott | |
| 8,216,189 B2 | 7/2012 | Stubbs | |
| 8,235,940 B2 | 8/2012 | Davis | |
| 8,715,219 B2 | 5/2014 | Stearns | |
| 9,138,549 B2 | 9/2015 | Pagel | |

(Continued)

FOREIGN PATENT DOCUMENTS

| EP | 1 109 486 | 5/2000 |
|---|---|---|
| EP | 2 825 840 | 9/2013 |
| WO | WO2013011398 | 1/2013 |

OTHER PUBLICATIONS

U.S. Appl. No. 15/293,013, filed Oct. 13, 2016.

*Primary Examiner* — Theodore J Stigell
(74) *Attorney, Agent, or Firm* — Baker Botts L.L.P.

(57) ABSTRACT

According to one embodiment, a method includes providing a trocar having a flow path for passage of an insufflation gas and also having a region outside the flow path that is open at the distal end of the trocar. The method also includes supplying insufflation gas through the flow path of the trocar and determining a differential pressure between a first pressure in the flow path of the trocar and a second pressure in the region of the trocar outside the flow path. The method also includes controlling the supply of insufflation gas through the trocar based at least in part on the determined differential pressure.

15 Claims, 4 Drawing Sheets

(56) References Cited

U.S. PATENT DOCUMENTS

2004/0102733 A1    5/2004   Naimark
2005/0115043 A1    6/2005   Maeshima
2012/0184897 A1    7/2012   Poll

* cited by examiner

METHOD AND SYSTEM FOR DETERMINING PRESSURE AND FLOW RESTRICTIONS IN A BODY CAVITY USING A TROCAR

TECHNICAL FIELD

The present disclosure relates generally to medical procedures and more particularly to a method and system for determining if a pressure or flow restriction occurs downstream of a gas delivery trocar flowing into a body cavity.

BACKGROUND

Laparoscopic surgery is a standard procedure in hospitals. Abdominal and chest cavity operations are being performed with instruments inserted through small incisions into interior portions of the patient. Such laparoscopic procedures are now considered the treatment of choice for operations such as the removal of the gall bladder, spleen, adrenal glands, uterus, and ovaries. These laparoscopic procedures are accomplished via access through a device typically known as a trocar.

A trocar facilitates the introduction of laparoscopic instruments into the abdomen or chest of the patient. These instruments are typically introduced into regions under fluid pressure. Providing a fluid into a body cavity is referred to as insufflation and the fluid, often a gas, is referred to herein as an insufflation gas. The purpose of using such a device is to inflate or distend the body cavity to (1) allow the surgeon to explore the area in which the surgery will be performed and (2) provide a view of the site to be treated or observed. These trocars typically also allow for the insertion of an instrument via the innermost tube of the trocar. Examples of one or more trocars are provided in U.S. Pat. No. 8,715,219 (the '219 Patent), U.S. Pat. No. 7,285,112 (the '112 Patent), and U.S. Pat. No. 8,216,189 (the '189 Patent), which are hereby incorporated by reference as if fully set forth herein.

Currently, insufflation is performed by providing a regulated pressurized insufflation gas to the peritoneal cavity via a cannula of the trocar. This insufflation gas, typically carbon dioxide, is supplied to a connection on the trocar tube by a flexible hose attached thereto by an insufflator. Accurate control of the pressure inside the body cavity is important because it can prevent loss of visualization thru the scope during the surgical procedure. Loss of visualization can slow down the surgery and is also potentially dangerous for the patient as the sharp surgical instruments can no longer be seen by the surgeon.

SUMMARY

According to one embodiment, a method includes providing a trocar having a flow path for passage of an insufflation gas and also having a region outside the flow path that is open at a distal end of the trocar. The method also includes supplying insufflation gas through the flow path of the trocar and determining a differential pressure between a first pressure in the flow path of the trocar and a second pressure in the region of the trocar outside the flow path. The method also includes controlling a supply of insufflation gas through the trocar based at least in part on the determined differential pressure.

According to another embodiment, a system includes a trocar having a flow path for passage of an insufflation gas and also having a region outside the flow path that is open at a distal end of the trocar. The system also includes a first pressure sensor being disposed in the flow path and a second pressure sensor being disposed in the region outside the flow path.

The teachings of the disclosure provide one or more technical advantages. Embodiments of the disclosure may have none, some, or all of these advantages. For example, in some embodiments, a method and apparatus allow detection of flow restrictions of an insufflator fluid to a body cavity, which is otherwise difficult to detect and such detection can prevent unsafe conditions arising as a result of the restrictions. Further, as a result of such detection, remedial action may be taken to properly control the supply of insufflation gas to the patient.

Other advantages will be apparent to those of skill in the art.

BRIEF DESCRIPTION OF THE DRAWINGS

For a more complete understanding of embodiments of the disclosure and the potential advantages thereof, reference is now made to the following written description taken in conjunction with the accompanying drawings, in which.

DETAILED DESCRIPTION OF THE DRAWINGS

The teachings of the present disclosure relate to a method for restriction discovery in an insufflation delivery system by monitoring a change in pressure at a trocar using two or more pressure sensors. Small pressure sensors are available in the marketplace that can measure absolute barometric pressures. The accuracy of these devices can be well less than one Pascal pressure. These small pressure sensors can be placed at various locations in or on a trocar that provides a conduit for delivery of insufflation gas to a body cavity. By placing two or more pressure sensors in the trocar, one sensor in the gas delivery stream (for example in an outer lumen of the trocar) and one sensor not in the gas stream (for example in the inner lumen of the trocar) a differential pressure between the two sensors can be determined. The teachings of the disclosure recognize that this differential pressure can be indicative of a restriction in the gas delivery.

When insufflation gas is flowing into the body cavity through the trocar, the pressure in the flow stream in the trocar (for example within an outer lumen) is higher than in the trocar outside the flow stream (for example within an inner lumen) and higher than the pressure downstream of the trocar. However, if a restriction occurs downstream of the trocar (for example when a veress needle attachment is utilized for initial insertion into a body cavity), the pressure within the flow stream in the trocar will equalize with the pressure outside the flow stream in the trocar, even when insufflation gas continues to flow into the body cavity.

Determining that this pressure has equalized by monitoring the pressure both within and outside the flow stream in the trocar allows discovery of undesirable restrictions, which would otherwise be difficult to detect. In one embodiment a control processor can make this determination and can also switch the gas flow delivery mechanism to safely deliver gas to the patient and allow for accurate pressurization of the body cavity. Example embodiments are best understood by referring to FIGS. 1A through 4 of the drawings and the description below, like numerals being used for like and corresponding parts of the various drawings.

Figure 1A:
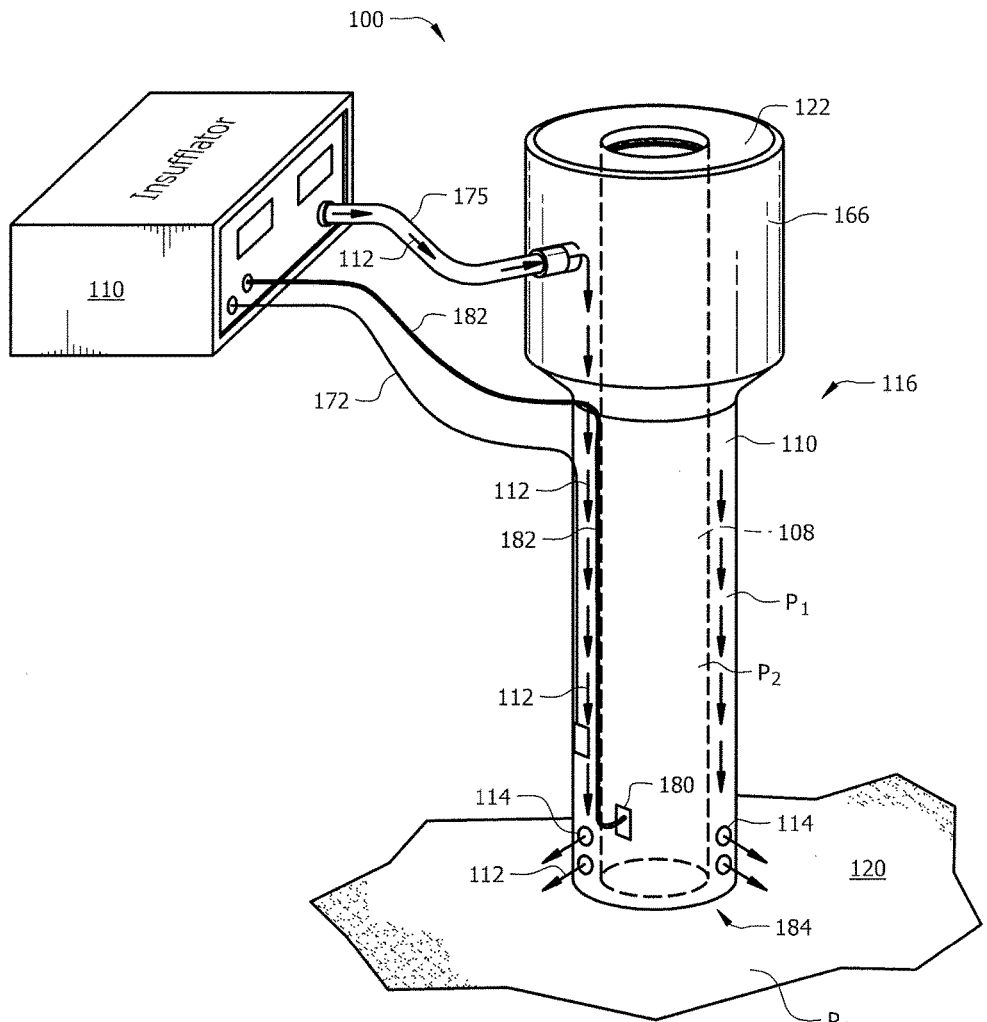
FIG. 1A is a schematic diagram illustrating a trocar having two pressure sensors.

FIG. 1A is a schematic diagram showing a system 100 that includes the distal end 184 of a trocar 116 placed in patient, or body, cavity 120. System 100 also includes an insufflator 110 connected to body cavity 120 through conduit 112 and trocar 116. Insufflator 110 controls the pressure within body cavity 120 during an operation by supplying insufflation gas through trocar 116 to body cavity 120. System 110, in this embodiment, also includes a conduit 175 for supplying insufflation gas to a portion of trocar 116. Pressure sensors 170 and 180 are disposed, in this embodiment, within trocar 116, and conductive connections 172 and 182, provide electrical connection between pressure sensors 170 and 180 and insufflator 110.

Distal end 184 of trocar 116 is inserted into body cavity 120 while the proximal end 122 allows an instrument 124 to be inserted such that trocar 116 provides access to body cavity 120 for the instrument 124. Suitable seals may be positioned in or around trocar 116 for preventing or reducing leakage of fluid out of trocar 116. Body cavity 120 may be accessed through an incision made with an obturator, which may be included in the same kit or package with trocars described herein.

Figure 1B:
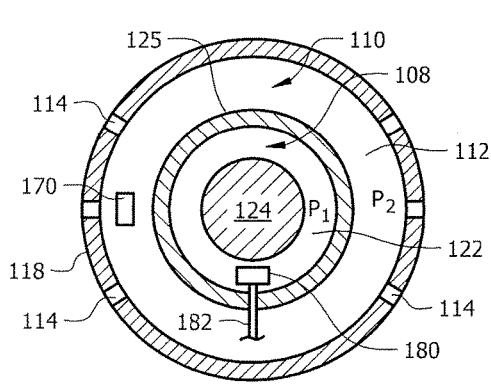
FIG. 1B is a cross sectional diagram showing a cross section of the trocar of FIG. 1A.

Trocar 116 is formed with an inner tubular member, or inner lumen, 108 and an outer tubular member, or outer lumen 110, in the embodiment of FIG. 1B. Inner lumen 108 is separated from outer lumen 110 by an inner wall 125. Outer lumen 110 is surrounded by an outer wall 118. Outer wall 118 may be formed with one or more holes or apertures 114 near a distal end 162 of trocar 116.

Insufflator 110 is a source of insufflation gas and may include appropriate control functionality for adjusting the supply of insufflation gas, such as in response to receiving signals indicative of the pressure in the body cavity. A surgical instrument 124 may be positioned within inner lumen 108 to allow access to body cavity 120 by a surgeon using surgical instrument 124. Electrical connections 172 and 182 may be electrical wires or any other suitable form of electrical connections.

Pressure sensor 170 is located at any point in the gas delivery path of trocar 116 and measures a pressure P2. Thus, in this embodiment, pressure sensor 170 is located in outer lumen 110. Pressure sensor 180, which measures a pressure P1, is located at any point out of the gas delivery path and is in intimate contact with the body cavity pressure (Pc). Thus, in this embodiment, pressure sensor 180 is located in inner lumen 108. Pressure sensors 170 and 180 may be absolute sensors that measure pressure and, for increased accuracy, can be calibrated against each other prior to surgical procedures. The measured pressure is communicated to insufflator 110 through electrical connection 182 through outer lumen 110, in this example. In one embodiment, pressure sensor 170 electrically couples to electrical connection 182 through apertures, although other forms of electrical coupling may be used, including wireless coupling.

When, for example, $CO_2$ gas is flowing from insufflator 110, pressure P2 will be higher than pressure P1 and Pc. This higher pressure is due to flow restrictions downstream of sensor 170. P1 and Pc are in intimate contact in this situation and hence P1 is equal to Pc allowing for an accurate pressure reading in body cavity 120. P1 can be used to accurately measure and control the pressure in body cavity 120. This allows for continuous gas delivery to body cavity 120 without having to stop the surgery and measure cavity pressure Pc.

Figure 1C:
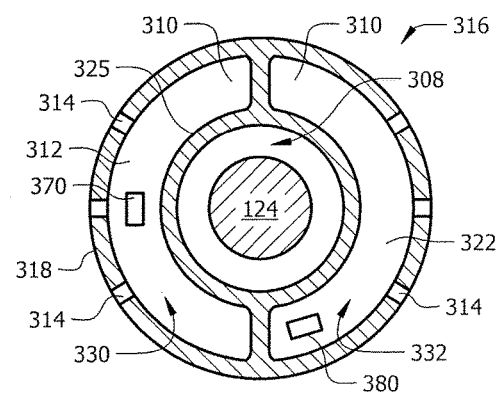
FIG. 1C is a cross sectional diagram showing a cross section of an alternative embodiment at the trocar of FIG. 1A.

FIG. 1C illustrates another embodiment of a trocar 316 that may be used in system 100. Trocar 316 has an inner lumen and an outer lumen with a plurality of chambers. Trocar 316 is analogous to trocar 116, with analogous portions having analogous reference numerals, except that trocar 316 is formed with an inner lumen 308 and an outer lumen 310 having a plurality of chambers 330, 332. Outer wall 318 is formed with one or more holes or apertures 314 near a distal end 362 of trocar 306 that are associated with chamber 330. Outer wall 118 may also be formed with one or more holes or apertures 315 proximate distal end 362 of trocar 306 that are associated with chamber 332. Conductive connection 382 may be disposed primarily in chamber 330, 332 of out lumen 310, in inner lumen 308, or in other suitable locations.

Providing separate chambers 330 and 332 in outer lumen 310 allows placement of pressure sensor 380 in one of the outer chambers 330, 332 and allows supplying insufflation gas in the other outer chamber 330, 332. This protects pressure sensor 380 from damage that could potentially be caused by instrument 124 due to insertion into inner lumen 108, while at the same time isolates pressure sensor 380 from supplied insufflation gas 312, which might otherwise adversely affect the accuracy of the pressure measured by pressure sensor 380. In general, measuring pressure by pressure sensor 380 in a location within trocar 380 that does not also provide a conduit for insufflation gas allows a more accurate estimation of Pc in body cavity 320 because flow of gas creates a pressure drop along its path. This pressure drop required for gas to flow would create inaccurate pressure readings at the pressure sensor 380.

Figure 2:
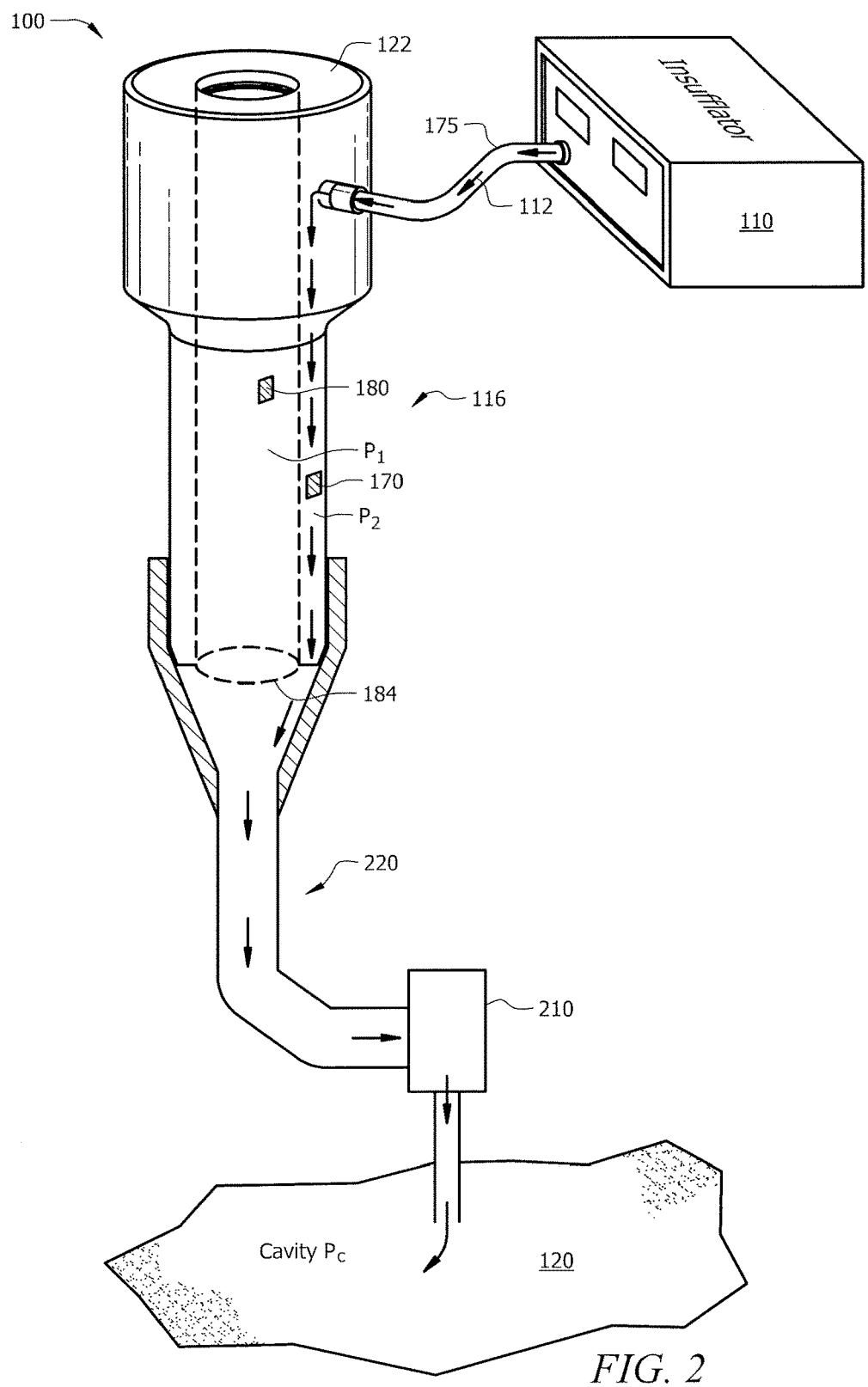
FIGS. 2 is a schematic diagram illustrating the trocar of FIG. 1A and also showing a restriction occurring downstream of the trocar, which is detected through use of the two pressure sensors of FIG. 1A.
Figure 3A:
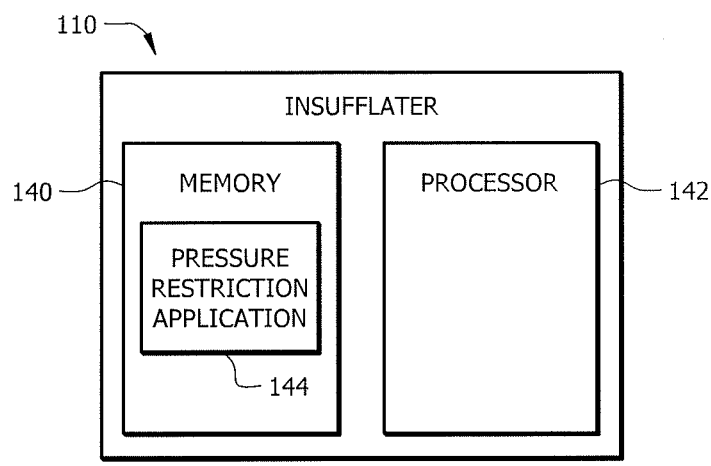
FIGS. 3A and 3B are block diagrams illustrating an insufflator with an integrated controller and an insufflator/controller system for controlling the supply of insufflation gas based on a pressure differential.
Figure 3B:
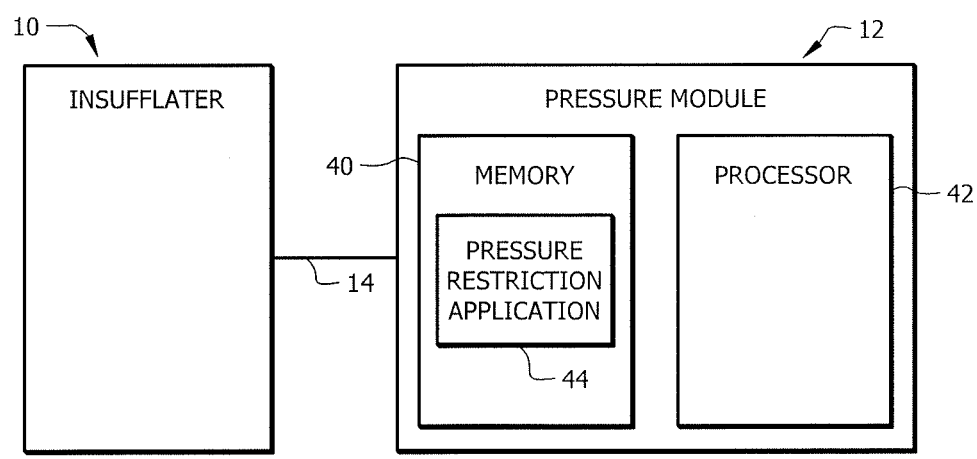
Figure 4:
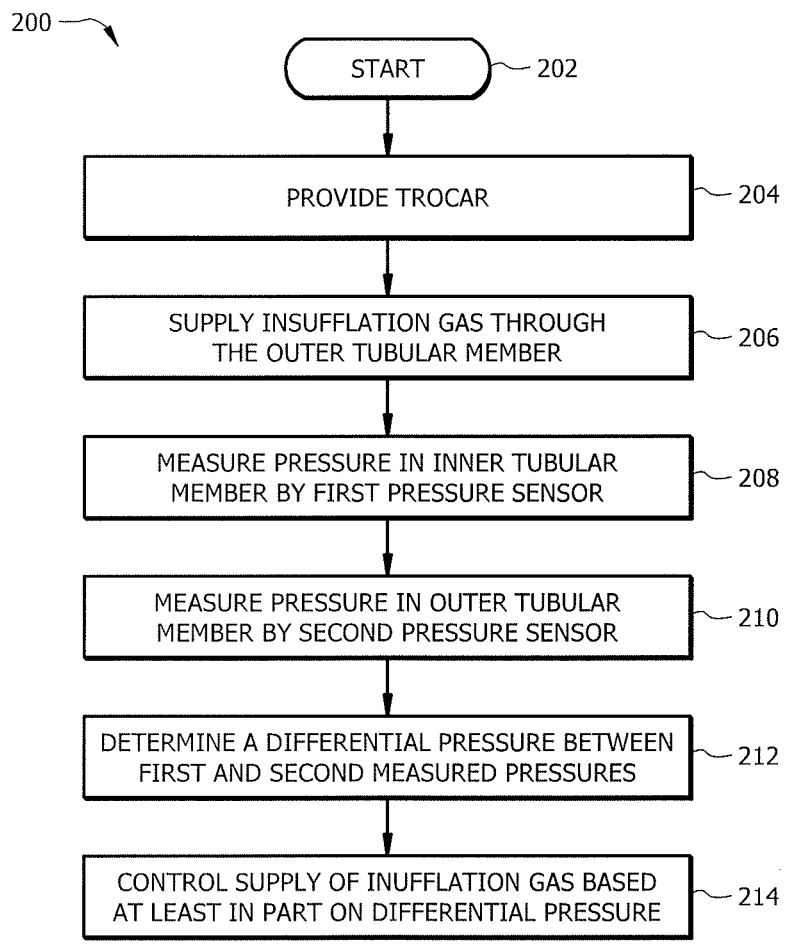
FIG. 4 is a flow chart illustrating a method for controlling the supply of insufflation gas based on a pressure differential between pressures measured by the two pressure sensors of the trocars in FIGS. 1A-2.

Additional details and embodiments of systems and methods for providing pressure control of the pressure in a body cavity are described below. FIG. 2 is a schematic diagram illustrating trocar 116 of FIG. 1A and also showing a downstream restriction, which is detected by use of two pressure sensors. FIGS. 3A and 3B illustrate example details of portions of the system of FIGS. 1A, according to one embodiment. FIG. 4 is a flow chart illustrating a method for determining pressure and flow restrictions in a body cavity using a trocar.

FIG. 2 is a schematic diagram illustrating trocar 116 of FIG. 1A and also showing a downstream restriction, which is detected by use of two pressure sensors. In particular, FIG. 2 shows trocar 116 connected to a veress needle 210. Trocar 116 and veress needle 210 are connected to each other via a tube 220 to ensure the insufflation gas is delivered to the body cavity 120. Due to the flow restrictions of veress needle 210, the gas pressure at P1 (outside the gas delivery path and measured by pressure sensor 180) and P2 (inside the gas delivery path and measured by pressure sensor 170) will equalize even when there is gas flowing. This equalized pressure may not be equal to the pressure in body cavity 120 since both pressure sensors 170, 180 are no longer in intimate contact with body cavity 120. Rather, the pressure at P1 and P2 will likely be higher than the pressure in body cavity 120. This can create an unsafe situation because insufflator 110 can no longer use P1 to accurately measure the cavity pressure Pc. Rather an alternate control mechanism to accurately measure pressure in body cavity 120 may be used. This alternate control mechanism can include periodically stopping gas flow from insufflator 110 to allow pressure to equalize to the pressure of body cavity 120 along the whole gas delivery path from insufflator 110. The pressure will equalize to the pressure of body cavity 120 and insufflator 110 can deliver gas accordingly based upon periodic pressure readings.

FIGS. 3A and 3B are block diagrams illustrating additional details of components of the system of FIGS. 1A-2 that may be used to effect pressure and flow restriction determination and resulting actions. FIG. 3A illustrates additional details of insufflator 110, according to one embodiment. In this embodiment, insufflator 110 includes a memory 140 and a processor 142 communicatively coupled to the memory 140. Memory 140 stores a pressure restriction application 144, which may include logic for effecting pressure and flow restriction determination as described herein with respect to the other FIGURES as well as control of the supply of insufflation gas to body cavity 120.

FIG. 3B illustrates an alternative embodiment of the system of FIGS. 1A-2 in which an insufflator 10 does not include the above desired pressure application and is communicatively coupled through a connection 14 to a pressure module 12. Pressure module 12 includes components analogous to those described with respect to FIG. 3A, but are included in this stand-alone pressure module 42. Connection 14 between insufflator 10 and pressure module 12 may be wired or wireless. It will be understood that although a software-based system is illustrated in FIGS. 3A and 3B the logic described herein could instead be implemented through hardware circuits or a combination of hardware and software.

FIG. 4 is a flow chart illustrating a method 200 that includes use of a pressure sensor associated with a trocar. The method may utilize structural items such as those described in FIGS. 1A through 3B or may use alternative structural items. Computational steps described below may be performed by any suitable computation device, including insufflator 110 and pressure module 12, for example.

The method begins at step 202. At step 204, a trocar is provided. The provided trocar includes an inner tubular member and an outer tubular member disposed about the inner tubular member, with a first pressure sensor disposed in the inner tubular member and a second pressure sensor being disposed in the outer tubular member. In alternative embodiments the first and separate pressure sensors are located in other portions of the trocar, with one being within the insufflation gas flow path and the other being outside the insufflation gas flow path. For example, in one embodiment one pressure sensor is located in a first chamber of an outside tubular member and the other pressure sensor is located in a second chamber of the outside tubular member. Also, in another embodiment, the insufflation gas could be supplied through the inner tubular member rather than through an outer tubular member.

Step 206 includes supplying insufflation gas through the gas delivery path, which in one embodiment may be through the outer tubular member. Step 208 includes measuring, by the first pressure sensor in the inner tubular member, a first pressure in the inner tubular member. Step 210 includes measuring, by the second pressure sensor in the outer tubular member, a second pressure in the outer tubular member. In step 212, a pressure differential between the pressure in the inner tubular member and the pressure in the outer tubular member is determined.

Based at least on the determined differential pressure, the supply of insufflation gas though the outer tubular member is controlled at step 214. This controlling of the supply of insufflation gas, may, in some embodiments, include determining that the pressure differential is below a threshold associated with a possible restriction downstream of the trocar and reducing supply of insufflation gas in response to determining that the pressure differential is below the threshold associated with the possible restriction downstream of the trocar. Such adjusting of the supply of insufflation gas may include reducing or increasing the supply of insufflation gas, as appropriate. In cases where a restriction is detected based on the differential pressure, a reduction in pressure is often advantageous. Such control may also include attempting to maintain a substantially constant pressure in a body cavity. The above-described control may be effected by an insufflator, such as insufflator 10 or 110, or other suitable control and gas supply apparatus(es).

The above steps may be performed in any desired order and may not necessarily be performed sequentially. For example, the pressure may be measured before, after, and/or during insertion of the surgical instrument. As another example, insufflation gas may be supplied before, during, and/or after pressure measurement.

Thus, the systems of FIG. 2A through 4 provide a way of detecting pressure and flow restrictions in the delivery of insufflation gas to a body cavity.

Additional details of systems 100 and 300 are described below for insufflation gas 102, insufflation gas source 170, trocars 116 and 316, open gas tubing connection 120, connection 164, conduit 175, conduit 185, and surgical instrument 124.

Insufflation gas 102 may be any suitable gas used for insufflation purposes. In one example, insufflation case is carbon dioxide. Insufflation gas source 170 may be any suitable source of insufflation gas 102 at any suitable pressure.

Trocars 116 and 316 may be any suitable as described herein. All trocars described herein may be open or closed at the distal end, as the application of the trocar would allow. Further, the trocars may or may not include apertures in their inner wall separating the outer lumen from the inner lumen. Further, all trocars described herein may be formed according to features described in the '219 Patent, the '112 Patent, and/or the '189 Patent. Further, trocars 116 and 316 may be formed with a heater and/or humidifier therein.

Conduit 175 may be any suitable conduit for providing an insufflation gas to a portion of a trocar. An example of conduit 175 includes flexible PVC tubing.

Surgical instrument 124 may be any suitable instrument that may be used in surgery, including an obturator used to make an incision to obtain access to a body cavity.

Modifications, additions, or omissions may be made to systems 100, 300 without departing from the scope of the invention. The components of these systems may be integrated or separated. Moreover, the operations of these systems may be performed by more, fewer, or other components.

Although FIGS. 2A through 4 have been described above as including particular steps and/or components, the method and systems of these FIGURES may include any combination of any of the described steps and/or components and any of the options or features described herein, as would be understood by one of ordinary skill in the art. For example, any of the steps, options, or features described herein may be utilized in combination with the illustrated embodiments of FIGS. 2A through 4 and/or any number of the other steps, options, or features also described herein, as would be understood by one of ordinary skill in the art.

Although the embodiments in the disclosure have been described in detail, numerous changes, substitutions, variations, alterations, and modifications may be ascertained by those skilled in the art. It is intended that the present disclosure encompass all such changes, substitutions, variations, alterations, and modifications.

What is claimed is:

1. A method comprising:
    providing a trocar having an inner tubular member and an outer tubular member disposed about the inner tubular member, a first pressure sensor being disposed in the inner tubular member and a second pressure sensor being disposed in the outer tubular member;
    supplying insufflation gas through the outer tubular member;
    measuring, by the first pressure sensor in the inner tubular member, a first pressure in the inner tubular member;
    measuring, by the second pressure sensor in the outer tubular member, a second pressure in the outer tubular member;
    determining, by at least one processor, a differential pressure between the first pressure and the second pressure; and
    controlling, by the at least one processor, the supply of insufflation gas through the outer tubular member based at least in part on the differential pressure between the first pressure and the second pressure.

2. The method of claim 1, wherein controlling, by the at least one processor, the supply of insufflation gas through the outer tubular member based at least in part on the differential pressure between the first pressure and the second pressure comprises:
    determining, by the at least one processor, that the pressure differential is below a threshold associated with a possible restriction downstream of the trocar; and
    reducing the supply of insufflation gas in response to determining that the pressure differential is below the threshold associated with the possible restriction downstream of the trocar.

3. The method of claim 1, wherein the first pressure sensor is electrically connected to an insufflator for supplying the insufflation gas, the electrical connection comprising a wire disposed at least partially within the inner tubular member of the trocar.

4. The method of claim 1, wherein controlling, by the at least one processor, the supply of insufflation gas through the outer tubular member based at least in part on the differential pressure between the first pressure and the second pressure comprises maintaining a substantially constant pressure in a body cavity.

5. The method of claim 1, wherein the second pressure sensor is electrically connected to an insufflator for supplying the insufflation gas, the electrical connection comprising a wire disposed at least partially within the outer tubular member of the trocar.

6. The method of claim 1, wherein the outer tubular member is formed with apertures in a side wall of the outer tubular member for allowing the insufflation gas to flow into a body cavity.

7. The method of claim 1, wherein the inner tubular member is formed with apertures in a side wall of the inner tubular member for allowing the insufflation gas to flow between the inner and outer tubular members.

8. A method comprising:
    providing a trocar having a flow path for passage of an insufflation gas and also having a region outside the flow path that is open at a distal end of the trocar;
    supplying insufflation gas through the flow path of the trocar;
    determining, by at least one processor, a differential pressure between a first pressure in the flow path of the trocar and a second pressure in the region of the trocar outside the flow path; and
    controlling, by the at least one processor, the supply of insufflation gas through the trocar based at least in part on the determined differential pressure.

9. The method of claim 8, wherein
    the trocar comprises an inner tubular member and an outer tubular member disposed about the inner tubular member;
    the flow path comprises the outer tubular member; and
    the region of the trocar outside the flow path comprises the inner tubular member.

10. The method of claim 8, wherein
    the trocar comprises an inner tubular member and an outer tubular member disposed about the inner tubular member;
    the flow path comprises the inner tubular member; and
    the region of the trocar outside the flow path comprises the outer tubular member.

11. The method of claim 8, wherein
    the trocar comprises an inner tubular member and an outer tubular member disposed about the inner tubular member, the outer tubular member comprising first and second chambers;
    the flow path comprises the first chamber of the outer tubular member; and
    the region of the trocar outside the flow path comprises the second chamber of the outer tubular member.

12. The method of claim 9, wherein a first pressure sensor is disposed within the flow path for measuring the first pressure within the flow path.

13. The method of claim 12, wherein a second pressure sensor is disposed within the region outside the flow path for measuring the second pressure in the region outside the flow path.

14. The method of claim 12, wherein the first pressure sensor is electrically connected to an insufflator for supplying the insufflation gas, the electrical connection comprising a wire disposed at least partially within the trocar.

15. The method of claim 8, wherein controlling, by the at least one processor, the supply of insufflation gas though the trocar based at least in part on the determined differential pressure comprises:
    determining, by the at least one processor, that the pressure differential is below a threshold associated with a possible restriction downstream of the trocar; and
    reducing the supply of insufflation gas in response to determining that the pressure differential is below the threshold associated with the possible restriction downstream of the trocar.

* * * * *